United States Patent [19]

Tunac

[11] Patent Number: 5,075,234
[45] Date of Patent: Dec. 24, 1991

[54] FERMENTOR/BIOREACTOR SYSTEMS HAVING HIGH AERATION CAPACITY

[76] Inventor: Josefino Tunac, 5284 Collington, Troy, Mich. 48098

[21] Appl. No.: 266,124

[22] Filed: Nov. 2, 1988

[51] Int. Cl.[5] .......................... C12M 3/02; C12M 1/06
[52] U.S. Cl. ...................................... 435/286; 435/296; 435/315; 435/316; 435/812; 435/818; 422/228; 366/102; 366/103; 261/122; 261/123; 55/178
[58] Field of Search ............... 435/284, 286, 288, 296, 435/313, 315, 316, 812, 813, 818; 422/135, 228; 261/122, 123; 210/219; 366/101–104, 106, 107, 307; 55/178

[56] References Cited

U.S. PATENT DOCUMENTS

| | | | |
|---|---|---|---|
| 3,298,615 | 1/1967 | Echols | 55/178 |
| 3,317,435 | 5/1967 | Yamashita et al. | 435/812 |
| 3,563,858 | 2/1971 | Worthington et al. | 435/812 |
| 4,036,699 | 7/1977 | Quigg | 435/315 |
| 4,382,685 | 5/1983 | Pearson | 435/316 |
| 4,649,114 | 3/1987 | Mittenburger et al. | 435/315 |
| 4,665,035 | 5/1987 | Tunac | 435/296 |
| 4,749,654 | 6/1988 | Karrer et al. | 261/122 |
| 4,870,018 | 7/1989 | Lehmann | 435/315 |

FOREIGN PATENT DOCUMENTS

| | | | |
|---|---|---|---|
| 0132877 | 8/1982 | Japan | 435/315 |
| 8502195 | 5/1985 | PCT Int'l Appl. | 435/315 |
| 1388419 | 4/1988 | U.S.S.R. | 435/313 |
| 1223418 | 2/1971 | United Kingdom | 435/315 |

Primary Examiner—David L. Lacey
Assistant Examiner—William H. Beisner
Attorney, Agent, or Firm—Krass & Young

[57] ABSTRACT

In concepts relating to biotechnology, fermentor and bioreactor apparatus and technology are provided for maximizing aeration for the cultivation and growth of aerobic microorganisms and tissue cells in artificial media such as aqueous growth media. The apparatus comprises a chamber with an impeller assembly for downward peripheral rotary flow under circumferential baffles that are downwardly disposed alongside microporous air sparger tubes. The agitation system preferably comprises a tree-turbine or a spherical-shaped impeller system. The apparatus provides advantages with respect to low shear, low power requirement, and high oxygen absorption rate, the latter being higher than conventional rates by an order of magnitude. In a preferred embodiment for the suppression of headspace foam, the invention comprises an assembly for forcing foam-destructive downdraft air into the headspace as well as stirrer or agitator assembly for stirring and breaking up foam that is present in the headspace.

16 Claims, 3 Drawing Sheets

FERMENTOR/BIOREACTOR SYSTEMS HAVING HIGH AERATION CAPACITY

TECHNICAL FIELD

This invention relates to biotechnology and more particularly to container apparatus and systems in which to cultivate and grow aerobic microorganisms and tissue cells in a sterile artificial environment, e.g., aqueous growth medium, and to novel methods of use employing the apparatus.

The vessel apparatus of the invention affords high aeration capacity through novel air sparging, dispersing and antifoamer systems. The high dispersion of air in the liquid medium is attainable at low agitation with the advantage of creating low shear thereby being favorable for the growth of shear-sensitive cells. The novel baffle, agitation and antifoamer systems enable the medium in the vessel to be mixed and aerated substantially more efficiently than heretofore possible by conventional means.

BACKGROUND OF THE INVENTION

In the early state of the art, fermentation processes were carried out on surfaces of solid media. However, surface fermentations are costly and difficult to operate. Thus, the liquid or submerged fermentation evolved. In submerged fermentation, particularly aerobic fermentation, air is an integral factor in the operation. The vessels used in submerged fermentation are called fermentors or bioreactors (the latter is preferably used when the vessel is designed for the culturing of tissue cells).

A fermentor is a vessel designed for the cultivation of microorganisms. The environment in the vessel is closely controlled to enable the proper expression of biochemical reactions for the production of the desired by-product. An important component for maintaining an aerobic environment is a system for gas dispersion and a means of transferring mass between the gas and the liquid phases. Fermentor design has not changed radically over the years, however, recently advances in biotechnology have spawned an array of compounds produced by microorganisms. User requirements are becoming increasingly sophisticated and complex, thus underscoring the need for improved culture vessels and systems.

To effect dispersion of air and media into the fermentation liquid and mixing therein, impellers are provided. The impellers used in fermentors are generally classified as flat-blade turbine (disc, vaned, and open), pitched-blade turbine or marine propeller. The marine propeller is essentially designed for mixing or suspending the solids in the medium, while the flat-blade turbine is for gas dispersion. Gas is efficiently dispersed when large gas-liquid interfacial surface areas per unit volume of the gas-liquid system are created.

When gas is sparged into the bottom of a vessel, the gas travels to the liquid surface as gas bubbles. These bubbles are relatively large and poorly distributed, particularly in the lower portion of the vessel. Since some interfacial areas are created by the gas as it rises to the surface, some mass transfer is possible. However, the contents of the vessel would likely be non-uniformly mixed because the only agitation is provided by the gas sparge.

When a gas bubble rises without being dispersed, the condition is known as flooding. To avoid flooding, the fermentor is equipped with a turbine agitator; the degree of dispersion is dependent on the speed of agitation. As the rotational speed is increased, bubbles are driven radially and eventually driven forcefully to the vessel wall and below the impeller. Thus, the horsepower required to prevent flooding is equivalent to that which is necessary to support minimum agitation. Turbine agitators for gas dispersion become larger and more power intensive with increasing liquid volume.

There are two basic ways in which an impeller can be used in the dual role of aeration and agitation. The first involves the use of a coaxial impeller in a tank without baffles; if the impeller turns fast enough, then a vortex is drawn down from the liquid surface to meet the impeller. This type of fermentor system is known as "vortex" aeration. The second system which is most commonly employed uses a series of vertical baffles (parallel to and spaced apart from the impeller) to prevent liquid swirl and thereby enables the impeller to create liquid turbulence.

The ultimate objective of gas dispersion or aeration is to maximize the oxygen absorption rate (OAR), i.e., for the oxygen to be transferred from the gas phase to the liquid, and from the liquid to the microbial cells. Because oxygen has a very low solubility (5.46 ml oxygen/liter) in aqueous culture solutions, it must be continuously supplied and dispersed. The impeller "breaks up" the air into small bubbles that are dispersed throughout the liquid. The agitation by the impeller can also aid in removing carbon dioxide and other metabolic gases from the medium. For mammalian and plant cell cultures, however, conventional agitation can cause contact damage (traumatic damage) to the cells. These tissue cells require low shear, and thereby gentle agitation for optimum growth. In this regard, the standard fermentor is not ideally designed for the cultivation of tissue cells.

A low shear condition is provided by the bubble column design. In a bubble column, air is simply bubbled or sparged into the liquid container. Thus, the bubble column has been modified for use as a fermentor/bioreactor. The resultant modifications include the tower and air-lift fermentors. In a tower fermentor, several perforated plates are placed in the column. Instead of perforated plates, motionless gas diffusors (stainless steel sheets bent into wave shape and put together with layers parallel to each other) can be used. Another type of tower fermentor involves addition of a recycling loop and the use of baffles.

The air-lift fermentor involves a draft "tube" submerged in the liquid medium inside the column. The air-lift fermentor applies air for circulating the medium: air and liquid flow concurrently upwards in one part of the column, resulting in a corresponding downward draft in another part. Another type of air-lift fermentor employs "pulsating aeration" in which air passes backward and forward through a single air filter. Recent variation in the air-lift fermentor involves a change in the shape of the vessel, particularly a tapered column instead of a cylindrical vessel. Despite these various improvements and despite the need for even more improved systems and technology, the same have not been available.

During the growth of a microbial culture in the fermentation vessel, particularly in an impeller agitated vessel, foaming is a recurring problem. Uncontrolled foaming may result in considerable loss of the fermentation/cultivation medium due to foam-over. Foaming may also lead to wetting of exhaust filters and consequent contamination of the batch or plugging of the filters. The factors that contribute to the formation of stable foams are relatively high surface tension and viscosity, and presence of finely divided solids.

Foaming may be controlled by mechanical means or by the addition of chemical antifoam agents. An example of a conventional mechanical foam breaking device is an array of specially shaped discs fitted on to the fermentor shaft. The foam is sucked into the discs and is destroyed by virtue of a weir arrangement. Other conventional means include a draught tube which acts as a weir for the liquid and foam to spill over; passing effluent air and foam through a nozzle at accelerated velocities, the resultant liquid being deflected down towards a pump for recycle into the fermentor (the system being limited however to solid-free cultures); and destruction of foam by ultrasonic waves, usually effective only at high air velocity.

Because of the limitations of existing mechanical foam breakers, chemical antifoam agents are more commonly used. The chemical agents act by competitively replacing the surface active agents responsible for causing the foam and themselves being unable to produce stable foams, e.g., silicones, polyglycol, and liquid paraffins. Although chemical antifoam agents are generally effective, certain microorganisms may be inhibited by such agents. Also, residual antifoam agents may interfere in the downstream processing of the fermentation broth.

OBJECTS OF THE INVENTION

It is therefore an object of the present invention to provide novel and improved systems for the growth and cultivation of microorganisms and tissue cells affording oxygen absorption rates and aeration capacity superior to conventional fermentors or bioreactors.

Another object of the invention is to provide improved mixing at low shear to prevent damage of shear-sensitive microorganisms and tissue cells.

Still another object is to provide means for suppression of headspace foam such that loss of culture medium, blockage of filters, and contamination of the culture are avoided.

These and other objects, features, and advantages of the invention will be seen from the following description and accompanying drawings.

SUMMARY AND DETAILED DESCRIPTION OF THE INVENTION

The invention in one preferred aspect concerns apparatus for maximizing aeration for submerged fermentation or tissue cell cultivation. The apparatus comprises a container vessel for aqueous growth medium, an impeller, and paired baffles in combination with microporous air spargers extending vertically in a downward sloping (preferably helical) configuration along the inner wall of the container vessel. The container vessel preferably is a barrel-type open-chamber container vessel having top and bottom ends and an inner side wall that is radially symmetrical about a central vertical axis. The impeller is coaxial with and rotatable about said vertical axis to cause continuous rotary or circumferential flow of aqueous medium contained in the vessel. The impeller generally may be of any suitable type providing radial flow, preferably made of stainless metal alloy, and in a preferred embodiment may be a single tree turbine impeller or disc turbine impeller or may comprise two or more such turbines in a stacked or tandem configuration, preferably a 4-blade turbine. A preferred impeller of a novel type affording improved mixing with low shear, is a dual or plural spherical shape impeller. Such an impeller can be provided by replacing each of the metal blades of a turbine impeller by an inert smooth or dimpled-surface ball, as described herein, the ball thus serving as a body having low fluid flow resistance.

The apparatus includes at least one diametrically opposed pair of elongated baffles for the inner side wall, preferably integral with the inner wall of the vessel. The baffles each extend and slope downward at the side wall (preferably in a helical configuration) in the direction of the radial flow, each baffle preferably being angled downwardly on a slope in the range from about 0.8 to 1.2. The baffles extend for a vertical distance sufficient to cause substantially complete downward rotary transport of the radially flowing aqueous medium.

The apparatus also includes a pair of diametrically opposed elongated air-supply hollow perforated conduit lines or spargers matching and extending adjacent to and parallel with said pair of baffles. The walls of the conduit lines are micro-permeable to passage of air therethrough such that baffle-directed aqueous medium while being transported downwardly may be aerated by air microbubbles permeating from said conduit lines. The spargers have a construction such that the permeation of microbubbles from the spargers into the aqueous medium is uniform throughout the length of each sparger. Each sparger or conduit line is located alongside its respective baffle, preferably at or adjacent to the upstream surface so that as the microbubbles are emitted from the sparger they are met by the downward radially flowing aqueous medium and are thus entrained in it and carried downward with the flow. In a preferred embodiment, the container vessel comprises four quadrilateral baffles subdividing the wall surface into four equal quadrants, and preferably for balanced sparging a pair of spargers is used alongside a respective pair of these diametrically opposed baffles.

To provide radial flow, the impeller can be top- or bottom-driven by suitable means which may be conventional. In one preferred embodiment featuring a bottom-drive analogous to drive means for a conventional kitchen blender, the apparatus comprises a base that includes drive means for driving engagement with the impeller. The container vessel bottom includes an open collar that is coaxial with the central axis of the vessel, and the collar and base comprise means for removably attaching the container vessel collar to the base, preferably by threadable or equivalent attachment, such that the drive means can readily be placed in or removed from driving engagement with the impeller.

The invention in another preferred aspect concerns a method of aerating aqueous growth medium for the cultivation of a selected aerobic microorganism or tissue cell. The method comprises the steps of charging aqueous growth medium with the selected microorganism or cell into a barrel-type open-chamber container vessel of given chamber depth having a chamber inner side wall that is radially symmetrical about a central vertical axis, causing the aqueous charge to flow radially and to rotate in the chamber continuously by rotating impeller means so that the aqueous charge moves from the laterally central portion of the chamber to the side wall of the chamber, causing the rotating charge at the side wall to flow downwardly by elongated downward (preferably helically) sloping baffle means so that the rotating charge is continuously carried downward to the bottom of the chamber, subjecting the thus downwardly-flowing charge to aeration by elongated porous sparger means that release microbubbles and are aligned (preferably parallel with) and generally coextensive in length with the elongated baffle means, allowing the thus aerated flowing charge and entrained microbubbles to release from the baffle at the chamber bottom and to centripetally return to and merge in the rotary flow with aqueous medium in the laterally central portion of the chamber, and further allowing the aqueous medium in said central portion to be transported and buoyed upward in the chamber by entrained microbubbles rising in the chamber.

The cycle of rotation, downward helical-baffled flow, aeration, centripetal flow, and buoyancy-assisted upward transport is repeated until the desired cultivation growth is achieved. A method that is preferred is one employing impeller means affording a high oxygen absorption rate, preferably a method employing a tree turbine impeller or a plural spherical shape impeller.

The invention in another preferred aspect concerns an apparatus and system for suppression of headspace foam in an aerated submerged fermentation or cell cultivation. The apparatus comprises for this purpose means, preferably fan means and especially top mount rotary fan means, centrally disposed over the headspace and adapted to force foam-destructive downdraft air into and substantially throughout the headspace. The apparatus also comprises stirrer or agitator means, preferably a co-axial rotary stirrer blade array preferably in rotary driven relation with the rotary fan means, adapted to physically contact and stir foam present in the headspace. The invention also concerns a method of aerating aqueous growth medium as described, and suppressing headspace foam, comprising the steps of forcing downdraft air into and substantially throughout the headspace and/or causing foam present in the headspace to be stirred.

BRIEF DESCRIPTION OF THE DRAWINGS

The invention will be more fully understood by reference to the accompanying drawings in which.

DETAILED DESCRIPTION OF THE INVENTION

Figure 1:
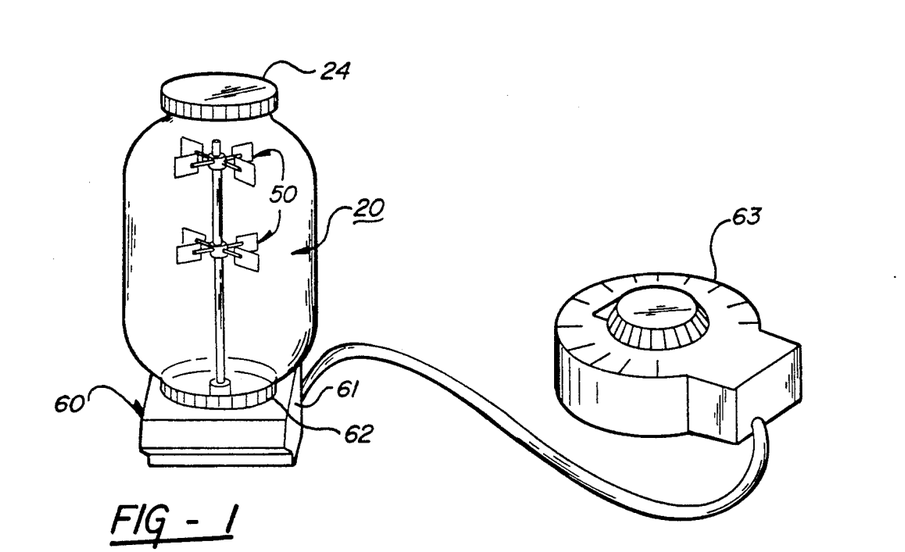
FIG. 1 is a view in perspective of a preferred embodiment of a fermentor/bioreactor according to the invention.
Figure 2:
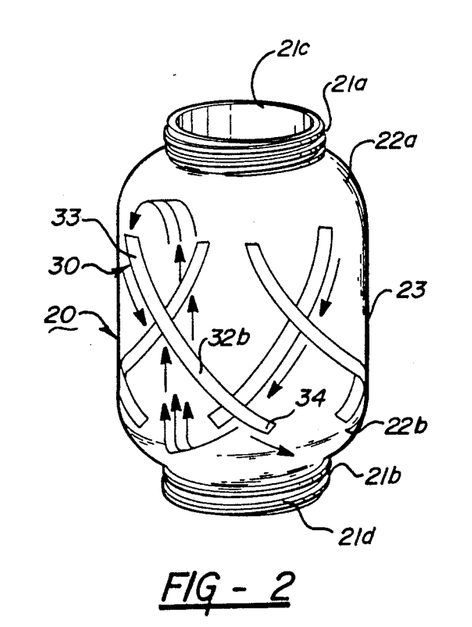
FIG. 2 is a perspective view of a container vessel according to the invention illustrating diametrically opposed helical baffling of the vessel in quadrants.
Figure 3:
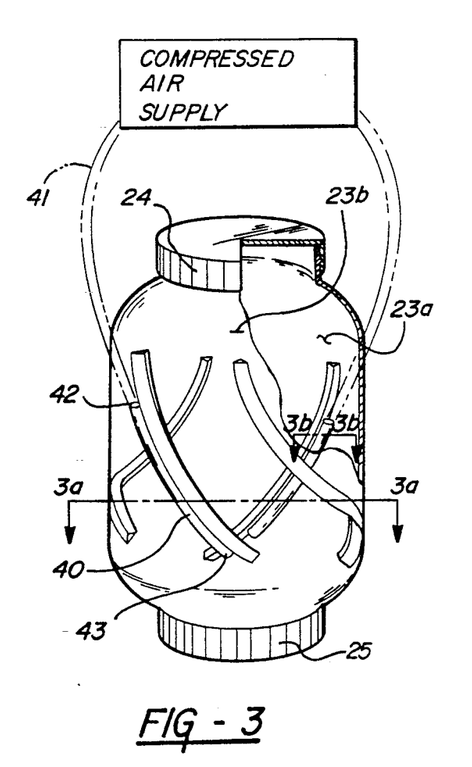
FIG. 3 is a similar view illustrating an opposed baffle pair in combination with a pair of helically disposed microporous sparger tubes.
Figure 3A:
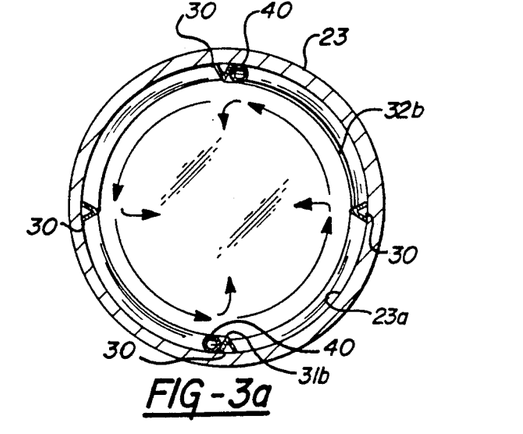
FIGS. 3a and 3b are cross-sectional views taken respectively on lines 3a—3b, 3b—3b of FIG. 3.
Figure 3B:
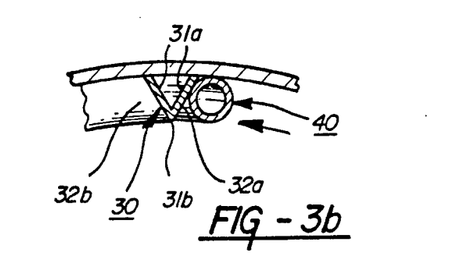

Referring to FIG. 1, the container vessel 20, fitted with bottom-drive disc impellers 50 and sealed with a top cover 24, is mounted for bottom-drive operation on a rotary drive unit 69 having a motor base 61 and mounting ring 62. The container vessel 20 as shown in FIG. 2 has top and bottom necks or collars 21a, 21b defining top and bottom openings 21c, 21d respectively. The vessel also has a side wall 23 and top and bottom shoulders 22a, 22b between which the interior of the vessel comprises a generally cylindrical open chamber encompassed by circumferential inner wall surface 23a. In preferred embodiments, the container vessel is made of autoclavable material such as glass or plastic especially transparent container material which facilitates viewing of the contents of the vessel (FIG. 3). The collars 21a, 21b are each provided with threaded surfaces (or equivalent surface) for threadable (or equivalent) attachment of the vessel to a cover 24 and a seating ring 25. As shown in FIGS. 2 and 3, the inner wall surface 23a serves as an attachment surface or base for a series of sloping or helically disposed baffles each of which slants or slopes downward from its top and 33 to its bottom end 34, these ends being located vertically within the shoulders 22a, 22b. In the preferred embodiment shown, the baffles 30 have a V-shape in cross section (FIG. 3a) and are arranged with equal circumferential spacing so that the inner wall surface is divided into four equal helically shaped parts or segments. As seen in FIG. 3b, the feet 31a of the baffle 30 are attached to the side wall by suitable means such as molding with the wall or by adhesive; the apex 31b forms a dividing line between a leading baffle surface 32a and a trailing baffle surface 32b. Located next to and alongside of the length of the leading surface 32a is a sparger tube 40. The top end 42 of the sparger tube is in open communication with an air supply line 41. The sparger tube bottom end 43 is closed. The vessel apparatus is designed to accommodate continuous rotary flow of aqueous growth medium filled into the container up to the fill line 23b.

Figure 4:
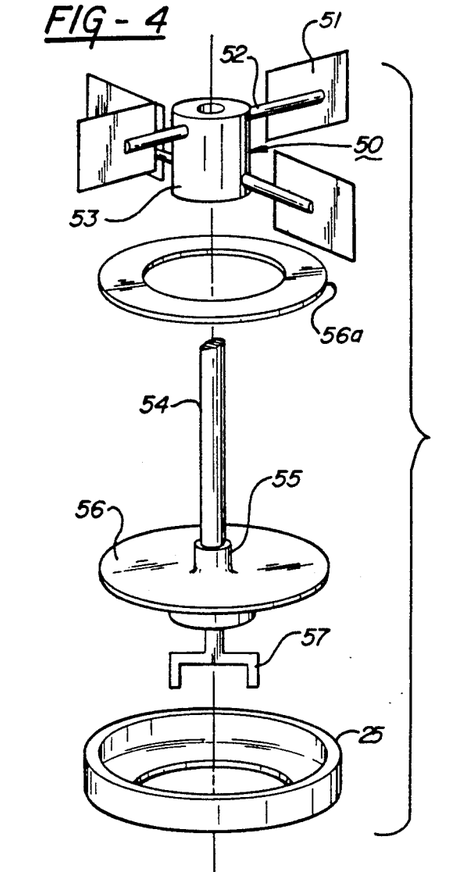
FIG. 4 is a view of bottom drive means and a hub-mount tree or 4-blade turbine impeller.
Figure 5:
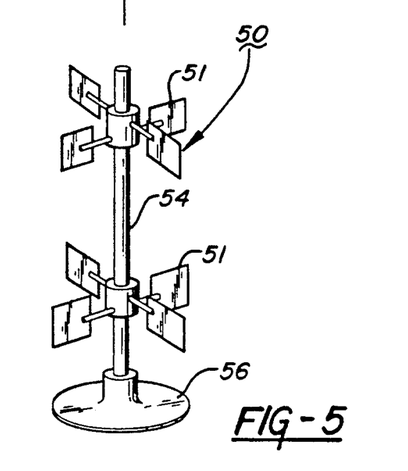
FIG. 5 is a view of a 4-blade turbine pair in tandem or stacked on a drive shaft according to a preferred embodiment of the invention.
Figure 6:
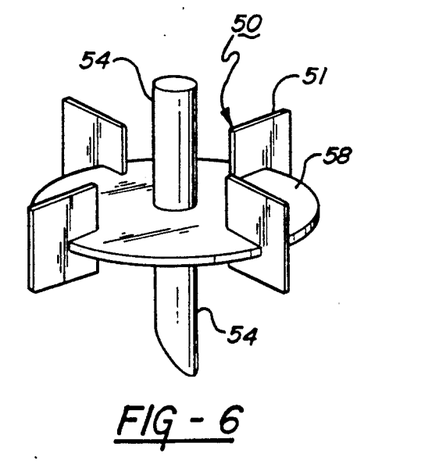
FIG. 6 is a view of a preferred 4-blade disk turbine of the invention.
Figure 7:
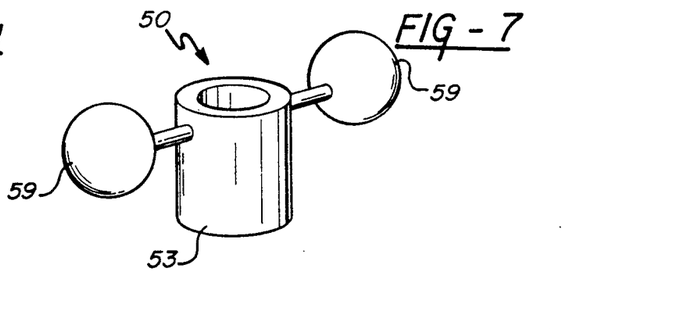
FIGS. 7 and 7a are views of a hub-mounted dual ball turbine impeller and a dual ball impeller pair 90 degree-offset mounted on the shaft, respectively, according to preferred embodiments.
Figure 7A:
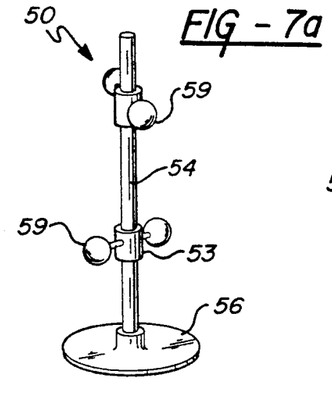

To provide rotary or circumferential flow of the aqueous medium, the apparatus in one preferred embodiment employs an impeller 50 (FIG. 4) which comprises impeller blades 51, arms 52, and hub 53. The hub 53 is carried on one end of a drive shaft 54 (by set-screw means, not shown) that extends through a bearing 55 and baseplate 56 to a drive yoke 57. For assembly, the baseplate with an overlying gasket 56a is seated into the seating ring 25, and the ring is threadably attached onto the bottom collar 21b of the container vessel in leak-proof relation. Other preferred impeller embodiments are represented by a stacked or tandem pair of 4-blade tree impellers (FIG. 5), a 4-blade disc impeller (FIG. 6), a dual plastic ball impeller (FIG. 7), and an offset or stacked pair of dual plastic ball impellers (FIG. 7a).

Figure 8:
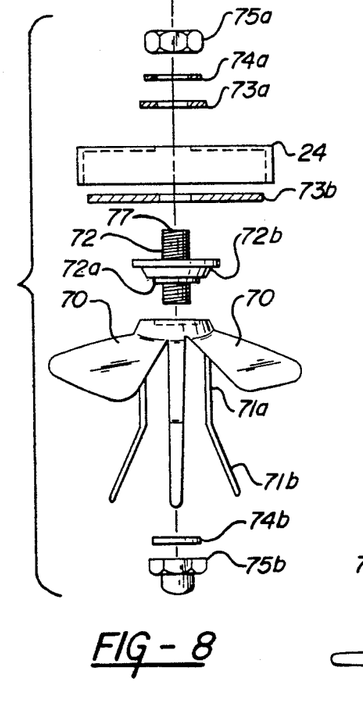
FIG. 8 is an exploded view of a top mount mechanical foam breaking apparatus according to a preferred embodiment of the invention.
Figure 9:
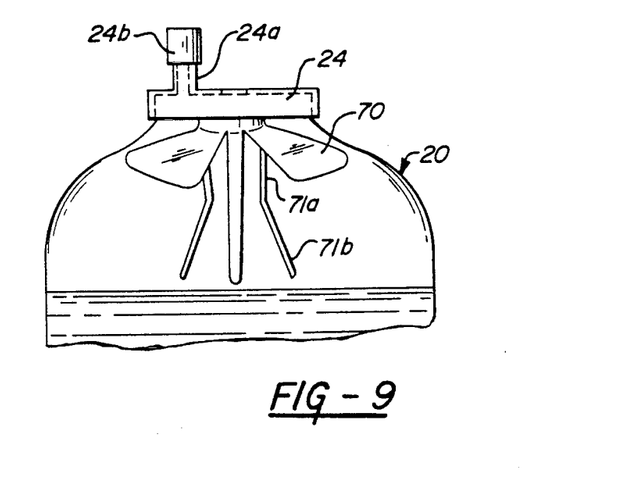
FIG. 9 is a side elevational view of the top portion of a container vessel showing the foam breaking apparatus mounted in the headspace of the container vessel.
Figure 10:
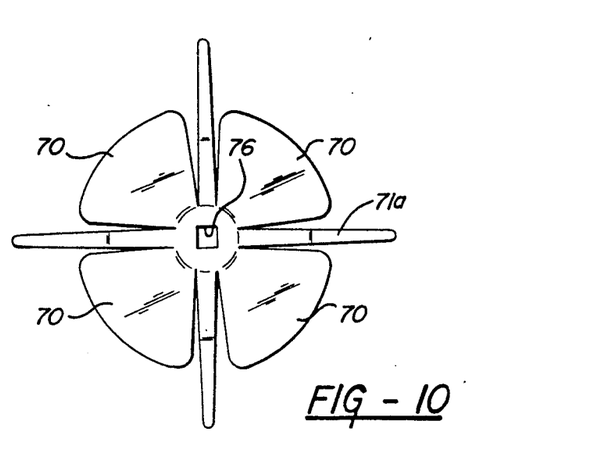
FIG. 10 is a view of a sheet material blank or cut-out from which the fan blades and stirrer arms of the foam breaking apparatus are formed.

As shown in FIGS. 8 and 9 in a preferred embodiment a top mount axial antifoamer mechanism is provided for the headspace of the container vessel. The mechanism, mounted through the center of the cover 24, includes fan blades 70, stirrer arms 71a and fingers 71b, a drive shaft 72, a fan mount 72a and a shaft bearing 72b, sealing gaskets 73a, 73b, washers 74a, 74b, and retention nuts 75a, 75b. The fan blade assembly includes a drive slot 76 which fits and is received around the fan mount 72a. The drive shaft 72 at its upper end is formed with a shaped axial recess serving at that end as a motor drive shaft collar 77 that receives and fits with a motor drive shaft (not shown) in fan-driving relation. The cover 24 includes an exhaust port 24a and an air filter 24b. As shown in FIG. 10, a sheet material cut-out or blank is provided. The blank is made of suitable material preferably of stainless metal and of a pliable yet rigid thickness such that it can be formed into a balanced array of blades 70 and stirrer arms 71a. As seen in FIG. 9, the arms 71a are bent or formed in mutually parallel relation and their finger portions 71b are bent outwardly at an angle.

In a typical culture growth operation, the apparatus is preliminarily sterilized (as by autoclaving). Part of the antifoamer mechanism (less the gaskets and cover 24) is installed in the vessel headspace to the position shown in FIG. 9, preferably by inserting the same through the bottom opening 21d, and the assembly is then completed by installing the gasket 73b, cover 24, gasket 73a, washer 74a and retention nut 75a. The elements of the container vessel are assembled and the vessel is mounted into the motor base 61 by means of the seating ring 25, motor base ring 62, and by engagement of the drive yoke 57 with the motor drive (not shown). The liquid growth medium (in volume at least sufficient to cover the spargers) is introduced to the container vessel by port means (not shown) in the cover 24 and the medium is seeded with a selected seed culture or tissue cell. The impeller drive is then set in motion at a desired continuous rate of counterclockwise rotation (as viewed from above) so that the aqueous medium is caused to flow in a continuous rotary or circumferential flow. The fan drive is also set in motion (preferably at high speed, e.g. 1500 rpm). Air under pressure is also supplied to the spargers. Thus, the liquid under the downwardly directing effect of the baffles, is directed downward extensively in the zone from the top shoulder 22a to the bottom shoulder 22b as illustrated in FIGS. 2 and 3a and is aerated by microbubbles escaping from the spargers. As the flow reaches the bottom ends 34 of the baffles, the flow is diverted laterally and centrally, and is returned and buoyed upwardly by the ascending microbubbles. Under action of the rotating impellers the rising aqueous medium is caused to move radially outward from the more central portions of the container chamber to the periphery where, again under the influence of the helically descending baffles, the radial flow is recycled downwardly and again aerated by microbubbles. The process is continued for a time sufficient to maximize aeration and to provide the desired endpoint of culture growth. During the operation, the tendency for foam to develop in the headspace is inhibited thereby avoiding loss of liquid medium through the exhaust port and also avoiding contamination and air filter blockage.

EVALUATION FOR AERATION CAPACITY

Preferred embodiments of the fermentor/bioreactor antifoamer apparatus of the invention were evaluated for aeration capacity employing an art-recognized sulfite oxidation method (cf. my U.S. Pat. No. 4,665,035).

For this comparison, the apparatus employed is described in what follows.

A. The Fermentor/Bioreactor Antifoamer Vessel.

A 1-gallon, plastic container was used as the container vessel. The bottom of the container was cut off and replaced with a threaded bottom of a blender jar (Vortex 7 Waring blender, Waring Products, New Hartford, Conn.), FIG. 2.

A quadrilateral array of four V-shaped plastic baffles (FIGS. 2, 3 and 3b) was secured by gluing in a downward helical or spiral pattern on the inside of the container. Each was 8.0" long, 0.5" deep, and the baffles were spaced 4.25" apart. The slope of the baffles was about 1.0.

B. The Aeration System.

Air was supplied by a laboratory air line, 15 psi. The air flow was determined by an air flow meter (Cole-Parmer Instrument Co., Chicago, Ill.)

Three different sparging systems were constructed for evaluation, a microporous tube sparger, a 12-pin sparger, and a 1-pin sparger:

1. "The porous tube sparger". Five-inch pieces of porous aerator tubes (POLYCYL plastics, Penn Plax, Garden City, N.Y.) were each secured alongside two opposite baffles. The open end of each tube was joined in open communication to a supply line manifold and an air source (FIG. 3).
2. "The 12-pin sparger". For each of two opposing baffles, plastic basketball inflater pins were drilled through the container wall and through the apex of the baffle. Six pins were drilled in a line on each baffle (1.25 inches apart). The stems of the pins were placed in open communication with a supply line manifold which was connected to an air source.
3. "The 1-pin sparger". As a control, one basketball inflater pin was drilled on the bottom of the plastic jar. The stem of the pin was connected to an air source. The one-hole sparger is the type of sparging system standard to most commercially available fermentors.

C. Agitation System.

The drive means employed for the impeller comprised the above-mentioned Waring blender including a motor drive, motor base and motor base ring. The blade assembly of the blender was replaced with a stainless steel shaft, 5/16"×7.0" FIG. 4. The speed of rotation in revolutions per minute was regulated by a variable speed transformer (Variable Autotransformer, Staco Energy Products, Co., Dayton, Ohio). The speed was determined by a digital tachometer Model HT-431, Ono Sokki, Japan).

D. Impeller Designs.

Different impeller systems were designed for the fermentor/bioreactor antifoamer:

1. The dual plastic ball impeller pair system, with the ball pairs offset from each other at right angles (FIG. 7a). Plastic golf balls (Pro-Fore Merchandisers, Inc., Grand Rapids, Mich.) were used to construct this impeller system. Two golf balls were fastened to the hub (FIG. 7) on opposite sides by bolt means to form a single plastic ball impeller.

2. The tree turbine impeller system. Two sets (FIG. 5) of hub-mounted turbine blades were used: two blades located ¼" from the hub top and the other two blades perpendicular to the first set and ¾" below (FIG. 4).
3. A standard disc turbine impeller (FIG. 6) was also evaluated. Two disc turbine impellers spaced apart on the shaft as in FIG. 5 were used.

AERATION CAPACITIES OF THE FERMENTOR/BIOREACTOR/ ANTIFOAMER

Aeration capacities was expressed as millimoles (mM) oxygen/L/min as determined by the sulfite oxidation method. For the test, the 1-gal fermentation vessel was filled with 3 liters of sulfite solution dissolved in tap water, 30° C.

A. Comparison of the Different Sparger Systems.

The different sparger systems (porous tube, 12-pin, and 1-pin) were compared for their efficacy in aerating the liquid. The impeller system used was the disc turbine. The air flow was set as 1 VVM (volume of air/volume of liquid/minute).

As shown in Table 1, the Porous Tube aerator system gave the best aeration values. The Porous Tube sparging system delivered multiple fine air bubbles to the liquid which allowed efficient dispersion of oxygen.

TABLE 1

Comparison of air spargers: single or 1-pin sparger, 12-pin sparger, porous tube aerator.

| Type of sparger | Oxygen absorption rate* (mM oxygen/L/min) | | |
|---|---|---|---|
| | 120 rpm | 200 rpm | 250 rpm |
| micro-porous tube | 4.18 | 9.55 | 13.22 |
| 12-pin | 0.90 | 1.46 | 3.12 |
| 1-pin | 0.58 | 1.22 | 2.29 |

*disc turbine impeller 1.5 VVM air flow

B. Comparison of the Different Impeller Systems.

Using the Porous Tube sparging system, the different impeller systems were evaluated. The Plastic Ball Impeller system gave relatively high aeration values, comparable with the values obtained from the Disc Turbine impeller system, particularly at the lower agitation speeds (Table 2). The Tree Turbine impeller system gave the highest aeration values.

TABLE 2

Comparison of impellers: "tree" turbine, disc turbine, and plastic ball impeller.

| | Oxygen absorption rate* (mM oxygen/L/min) | | |
|---|---|---|---|
| RPM | plastic ball impeller | disc turbine | "tree" turbine |
| 75 | 3.38 | 2.45 | 3.43 |
| 100 | 3.91 | 3.90 | 4.93 |
| 125 | 4.44 | 5.52 | 6.42 |
| 150 | 4.97 | 7.04 | 7.91 |
| 175 | 5.51 | 8.57 | 9.41 |
| 200 | 6.03 | 10.11 | 10.90 |
| 225 | 6.56 | 11.64 | 12.39 |
| 250 | 7.09 | 13.17 | 13.89 |
| 275 | 7.63 | 14.70 | 15.38 |
| 300 | 8.15 | 16.23 | 16.87 |

*air flow = 1.5 VVM

C. Comparison of Aeration Levels.

Different conventional fermentation systems were evaluated for their aeration capacities. Of these fermentors, the highest aeration value was obtained from a 200-gal fermentor, a value of 4.1 mM oxygen/L/min at 250 rpm (Table 3).

TABLE 3

| Type of fermentor | Aeration capacity. Comparison with conventional fermentors. | | | | | | |
|---|---|---|---|---|---|---|---|
| | 100 rpm | 150 rpm | 200 rpm | 250 rpm | 300 rpm | 350 rpm | 450 rpm |
| New Brunswick | — | — | — | — | 1.4 | — | — |
| Biolafitte (30-L) | — | — | — | — | — | — | 2.4 |
| Parke-Davis (30-L) | — | — | 0.8 | 1.5 | 2.0 | 2.3 | — |
| (200-gal) | — | 2.2 | 3.2 | 4.1 | — | — | — |
| Fermentor/Bioreactor combining Helical baffle flow plus porous tube sparger: | | | | | | | |
| Plastic ball impeller | 3.9 | 4.9 | 6.0 | 7.1 | 8.2 | — | — |
| Tree turbine | 4.9 | 7.9 | 10.9 | 13.9 | 16.9 | — | — |
| Disc turbine | 3.9 | 7.0 | 10.1 | 13.2 | 16.2 | — | — |

*Air flow = 1.25-1.50 VVM

The aeration values of the conventional fermentors were well exceeded by those of the present fermentor/bioreactor.

MIXING PATTERN, SHEAR, POWER REQUIREMENT AND FOAM BREAKING EFFICIENCY

The present spiral design baffle system enabled a downward flow motion of the agitated liquid. Such downward flow pattern is usually afforded by the conventional marine propeller impeller which typifies a good mixing system.

The plastic ball impeller system afforded high aeration capacity at low shear. This impeller system, therefore, is particularly advantageous as an agitation system for shear-sensitive cells.

The relative power requirement of the three impeller systems were evaluated by determining the actual RPM of the shaft. Of the three impeller systems, the plastic ball spherical impeller of this invention drew the least power (Table 4):

TABLE 4

Actual RPM (revolution/min) of the agitation shaft with 3 impeller systems at different speed settings.

| Autotransformer speed setting* | Actual speed, rpm | | |
|---|---|---|---|
| | Spherical impeller | Disc turbine | Tree turbine |
| 20 | 115 | 90 | 65 |
| 25 | 160 | 125 | 95 |
| 30 | 220 | 200 | 145 |
| 35 | 280 | 230 | 195 |
| 40 | 300 | 240 | 200 |

*3 liters of water load in the 1-gal fermentation vessel.

The efficacy of a preferred antifoamer device of the invention was tested on a liquid soap foam. For this, liquid soap was added into the liquid in the fermentor and extensive foaming was created once the liquid was mixed. Upon formation of foam, the antifoamer device was operated at 1500 rpm (a suitable commercial motor is a Model 7 Mixette, Hamilton Beach, Racine, Wis.) with the result that the foam buildup was promptly destroyed and further buildup was effectively suppressed.

The container apparatus of the invention can be made of any suitable materials which may be conventional materials used in biocompatible container stainless metal alloy, glassware, or plasticware technology (e.g., see U.S. Pat. No. 4,720,462, incorporated herewith). A preferred container embodiment is a unitary polysulfone, or polycarbonate plastic or similar plastic container baffled as illustrated in FIG. 1, suitable for sterilization and reuse or being disposable. The shape and size of the apparatus are not particularly critical. A wide range of sizes can be used as required by laboratory and industrial needs.

While the invention is described in detail in the foregoing specification, it will be realized by those skilled in the art that considerable variation can be made in such detail without departing from the spirit and scope of the claims which follow.

I claim:

1. Apparatus for maximizing aeration for submerged fermentation or tissue cell cultivation, comprising:

an open-chamber container vessel for aqueous growth medium having top and bottom ends and an inner side wall that is radially symmetrical about a central vertical axis;

impeller means co-axial with and rotatable about said axis to cause continuous radial flow of aqueous medium contained in the vessel;

at least one pair of diametrically opposed elongated helical baffles on the inner side wall, each of said baffles being slanted downward adjacent the side wall for a vertical distance sufficient to cause downward rotary transport of the radially flowing aqueous medium contained in the vessel; and at least one pair of diametrically opposed elongated air supply conduit lines or spargers matching and extending adjacent to and substantially parallel with said at least one pair of baffles, the walls of the conduit lines being micropermeable to passage of air therethrough such that baffle-directed aqueous medium while being transported downwardly can be aerated by air microbubbles permeating from said conduit lines.

2. The apparatus of claim 1 wherein the impeller means comprises a 4-blade tree turbine.

3. The apparatus of claim 1 wherein the impeller means comprises a 4-blade disc turbine.

4. The apparatus of claim 1 wherein the impeller means comprises a dual spherical shape turbine impeller.

5. The apparatus of claim 1 wherein each of said baffles is molded or adhesively attached with the side wall.

6. The apparatus of claim 1 wherein each of said baffles is angled downwardly on a slope with respect to horizontal in the range from about 0.8 to 1.2.

7. The apparatus of claim 1 wherein said at least one pair of baffles comprises another pair of said diametrically opposed baffles, all of said pairs of baffles being arranged so as to subdivide the inner side wall into four equal quadrants.

8. The apparatus of claim 1 wherein said at least one pair of diametrically opposed conduit lines or spargers extend substantially throughout the length of each of the respective baffles of said pair of baffles.

9. The apparatus of claim 1 comprising a plurality of pairs of said diametrically opposed baffles and a matching plurality of pairs of said diametrically opposed conduit lines or spargers, wherein each of said pairs of conduit lines or spargers is located adjacent to each of said baffles of said respective baffle pairs.

10. The apparatus of claim 1 wherein each of said baffles has a V-shaped cross-section.

11. The apparatus of claim 10 wherein the V-shaped cross-section of each of said baffles has a leading or upstream surface substantially throughout the length of the baffle presented to the rotary transport of aqueous fluid contained in the vessel.

12. The apparatus according to claim 1 wherein the vessel top end defines a headspace and the apparatus further comprises foam suppression means centrally disposed over said headspace for forcing downdraft air into and substantially throughout said headspace.

13. The apparatus according to claim 12 wherein said foam suppression means comprises a rotary fan means for forcing downdraft air into and substantially throughout said headspace, a co-axial rotary stirrer blade array for contacting and stirring foam present in said headspace, and rotary drive means in drivable engagement by common drive shaft means with said fan means and said stirrer blade array.

14. The apparatus of claim 1 wherein the vessel bottom end comprises an open collar that is co-axial with the central axis.

15. The apparatus of claim 14 wherein said impeller means is removable attached to said open collar.

16. The apparatus of claim 15 wherein said impeller means is threadably attached to said open collar.

* * * * *

UNITED STATES PATENT AND TRADEMARK OFFICE
CERTIFICATE OF CORRECTION

PATENT NO. : 5,075,234

DATED : December 24, 1991

INVENTOR(S) : Josefino Tunac

It is certified that error appears in the above-identified patent and that said Letters Patent is hereby corrected as shown below:

Column 12, line 46, change "removable" to --removably--.

Signed and Sealed this

Twenty-seventh Day of April, 1993

Attest:

MICHAEL K. KIRK

*Attesting Officer*     *Acting Commissioner of Patents and Trademarks*